United States Patent
Cewers

Patent Number: 5,816,242
Date of Patent: Oct. 6, 1998

[54] DEVICE FOR TRANSMITTING INFORMATION VIA A PATIENT TUBE IN AN INTENSIVE CARE OR ANESTHETIC MACHINE

[75] Inventor: Göran Cewers, Lund, Sweden

[73] Assignee: Siemens Elema AB, Solna, Sweden

[21] Appl. No.: 636,519

[22] Filed: Apr. 23, 1996

[30] Foreign Application Priority Data

May 5, 1995 [SE] Sweden ................................. 9501678

[51] Int. Cl.$^6$ ............................ A61B 5/08; A61M 16/00; A62B 7/00; F16K 1/02
[52] U.S. Cl. ............................... 128/204.21; 128/200.24; 128/203.12; 128/912; 600/539; 600/532; 600/538; 607/60; 607/62; 73/861.25
[58] Field of Search ...................... 128/204.21, 204.22, 128/205.23, 200.24, 203.12, 912; 600/438, 533, 534, 529, 532, 538, 539; 73/861.25; 607/60, 62

[56] References Cited

U.S. PATENT DOCUMENTS

| | | |
|---|---|---|
| 3,974,681 | 8/1976 | Namery . |
| 4,227,407 | 10/1980 | Drost ..................................... 73/194 A |
| 4,248,085 | 2/1981 | Coulthard ............................. 73/861.05 |
| 4,320,666 | 3/1982 | Redding ................................ 73/861.28 |
| 4,423,739 | 1/1984 | Passaro et al. ...................... 128/204.22 |
| 4,484,478 | 11/1984 | Härkönen ............................. 73/861.06 |
| 4,648,396 | 3/1987 | Raemer ................................ 128/204.22 |
| 4,712,566 | 12/1987 | Hok . |
| 4,754,650 | 7/1988 | Smalling et al. ..................... 73/861.28 |
| 4,856,321 | 8/1989 | Smalling et al. ..................... 73/40.5 A |
| 4,936,310 | 6/1990 | Engstrom et al. . |
| 4,989,609 | 2/1991 | Smith et al. . |
| 5,018,529 | 5/1991 | Tenerz et al. . |
| 5,020,528 | 6/1991 | Myers . |
| 5,113,859 | 5/1992 | Funke ............................... 128/419 PG |
| 5,121,639 | 6/1992 | McShane ............................. 73/861.06 |
| 5,156,157 | 10/1992 | Valenta, Jr. et al. ............... 128/662.06 |
| 5,214,966 | 6/1993 | Delsing ................................ 73/861.28 |
| 5,289,436 | 2/1994 | Terhune . |
| 5,551,953 | 9/1996 | Lattin et al. ............................. 604/20 |

FOREIGN PATENT DOCUMENTS

| | | | |
|---|---|---|---|
| 145384 | 6/1985 | European Pat. Off. .......... 128/204.22 |
| WO 92/03724 | 3/1992 | WIPO . |

OTHER PUBLICATIONS

Operating Manual for Siemens Co$_2$ Analyzer 930, ©1981. Siemens–Elema AB, Life Support Syst., Mktg. Com's., Solna, Sweden #6978803 E313E.

*Primary Examiner*—Kimberly L. Asher
*Attorney, Agent, or Firm*—Hill & Simpson

[57] ABSTRACT

In a device for transmitting information via a patient tube from a location near the patient to an intensive care or anesthetic machine, at least one signal source is arranged at one end portion of the tube to deliver information-carrying signals which propagate longitudinally through the medium inside the tube. At least one receiver is arranged at the other end of the tube to receive the signals.

25 Claims, 2 Drawing Sheets

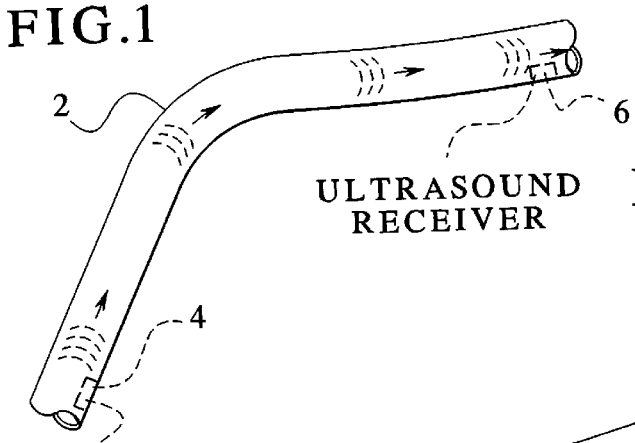
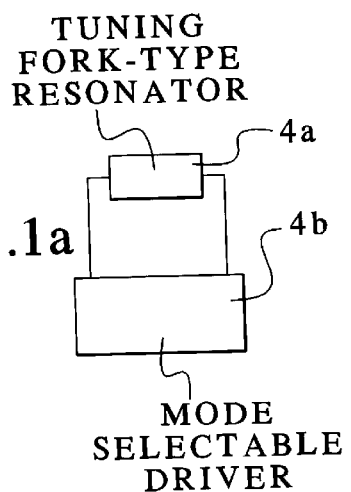
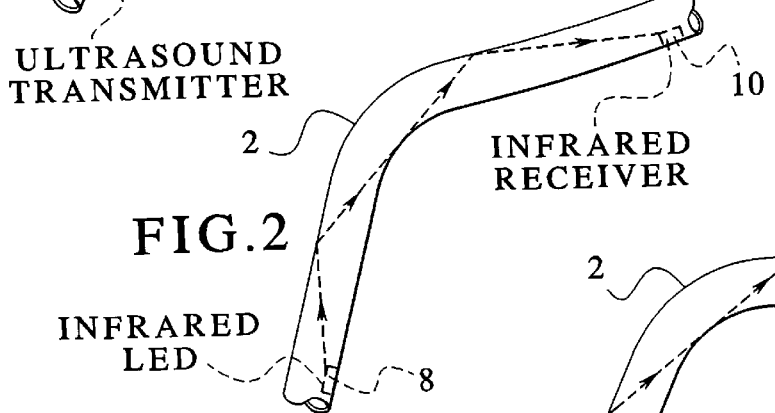
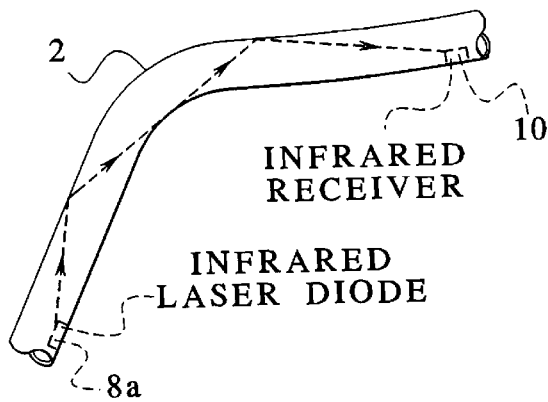
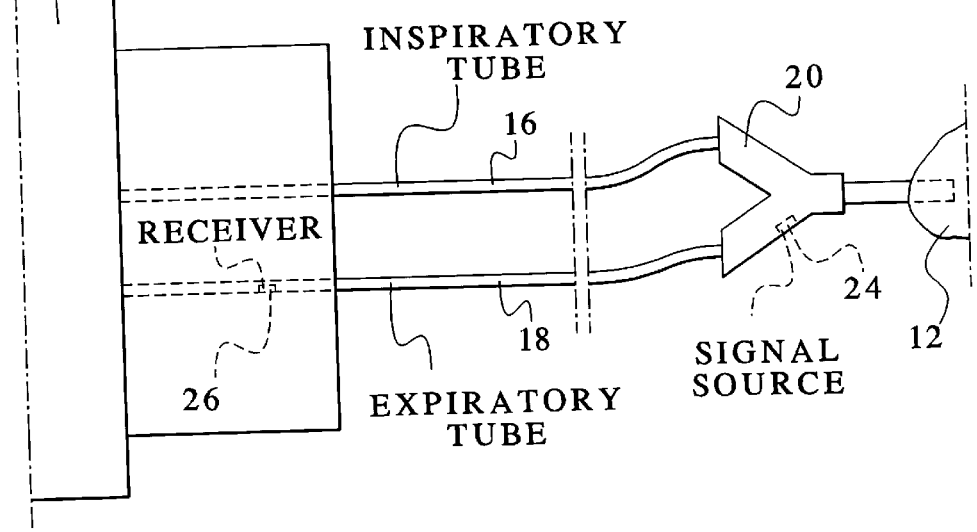

DEVICE FOR TRANSMITTING INFORMATION VIA A PATIENT TUBE IN AN INTENSIVE CARE OR ANESTHETIC MACHINE

BACKGROUND OF THE INVENTION

1. Field of the Invention

The present invention relates to a device for transmitting information via a patient tube in an intensive care or anesthetic apparatus.

2. Description of the Prior Art

When intensive care and anesthetic units are used, they are normally located at a distance from the patient, and the patient is connected to the equipment by one or more tubes. The operator of the machine is often near the patient, making it difficult for her or him to operate the machine and select its functions from the instrument panel. The instrument panel, in turn, is often located at a distance from the machine. Examples of functions which the operator may wish to activate at the same time as she or he is next to the patient are $O_2$ flushing, alarm check, fast changes in the anesthetic dose or respiratory pattern, etc.

Known equipment of this type has hitherto employed some kind of transducer arranged near the patient, e.g. in the Y-piece of the patient's tubes. $CO_2$ transducers are examples of one such transducer which must be located near the patient. These transducers are connected to the machine itself by a separate cord for transmitting measurement signals. This additional cord complicates the use of the equipment.

The cord can alternatively be attached to the exterior of the patient tube, or a conductor can be arranged in the tube wall to transmit the signals, but this complicates the equipment and makes it more complex to set up.

SUMMARY OF THE INVENTION

An object of the present invention is to eliminate the aforementioned shortcoming in the known intensive care and anesthetic machines.

The above object is achieved in a device according to the invention, wherein communication between the patient end of the patient tube and the machine take place via the medium inside the tube, thus the need for a special cord or conductor for signal transmission is eliminated. In addition, information is transmitted inside the patient tube and the transmission is accordingly insulated from the surroundings, i.e. neighboring equipment is not disturbed. Moreover, neither noise nor unintentional operating orders outside the tube can affect the transmission of information inside the tube.

In embodiments of the device according to the invention, the signal source can be a source of ultrasound or infrared light arranged inside the tube. The signal source can be controlled with a control unit, e.g. to connect and disconnect the signal source, arranged outside the tube. The signal source can alternatively be connected to an electronics unit, detachably arranged on the exterior of the tube, for controlling the signal source. The electronics unit is then devised so it can easily be detached from the tube, and the tube with the signal source can then be autoclaved. The electronics unit can also be made autoclavable.

In other embodiments of the device according to the invention, the ultrasound transducer includes an electrically or mechanically excitable acoustic resonator, and the ultrasound transducer appropriately has a frequency which is less than 100 kHz. Ultrasound readily propagates in most anesthetic gases, although the attenuation is strong in nitrous oxide at frequencies above 100 kHz, so selection of a lower frequency is appropriate.

According to another embodiment of the device of the invention, the signal source is arranged to emit a frequency modulated, amplitude modulated, phase modulated or time modulated signal, thereby permitting a more advanced transmission of information.

According to yet another embodiment of the invention, the signal source includes an activatable, mechanical, tuning fork-type transducer, preferably arranged to supply at least two tones, thereby increasing the reliability in the communication.

In another embodiment of the invention, the receiver is arranged at the machine end of the tube, which is connected to the intensive care or anesthetic machine. The receiver is then preferably supplied with power from the intensive care or anesthetic machine, so no battery is needed to supply power to the receiver.

According to a further embodiment of the invention, the signal source is arranged in an intermediate piece connectable to the patient tube. The intermediate piece is disposed at the patient end of the tube to be connected to the patient mouthpiece.

In another embodiment of the invention, the signal source and the receiver are arranged inside the expiratory tube of the intensive care or anesthetic unit, which is preferred for hygienic reasons.

In a further embodiment of the invention, a signal source and a receiver are arranged at both ends of the tube for two-way information transmission through the tube. This makes it possible to, e.g., measure a flow near the patient and to control, via the intensive care or anesthetic machine, a valve, also arranged adjacent the patient, according to the measured flow. The flow can be measured with a separate flow meter or be determined from the Doppler shift in a signal frequency, caused by the flow of the medium in the tube.

DESCRIPTION OF THE DRAWINGS

FIGS. 1 and 2 and 2a illustrate the principles of the device according to the invention, for an ultrasound embodiment (FIG. 1) and an infrared light embodiment (FIGS. 2 and 2a). FIG. 1a is a schematic illustration of an embodiment for the ultrasound transmitter of FIG. 1.

FIG. 3 schematically illustrates how a patient is connected to an intensive care or anesthetic machine via inspiratory and expiratory tubes with the signal source and receiver arranged in Y-pieces at the ends of the tube in accordance with the invention.

DESCRIPTION OF THE PREFERRED EMBODIMENTS

Figure 4:
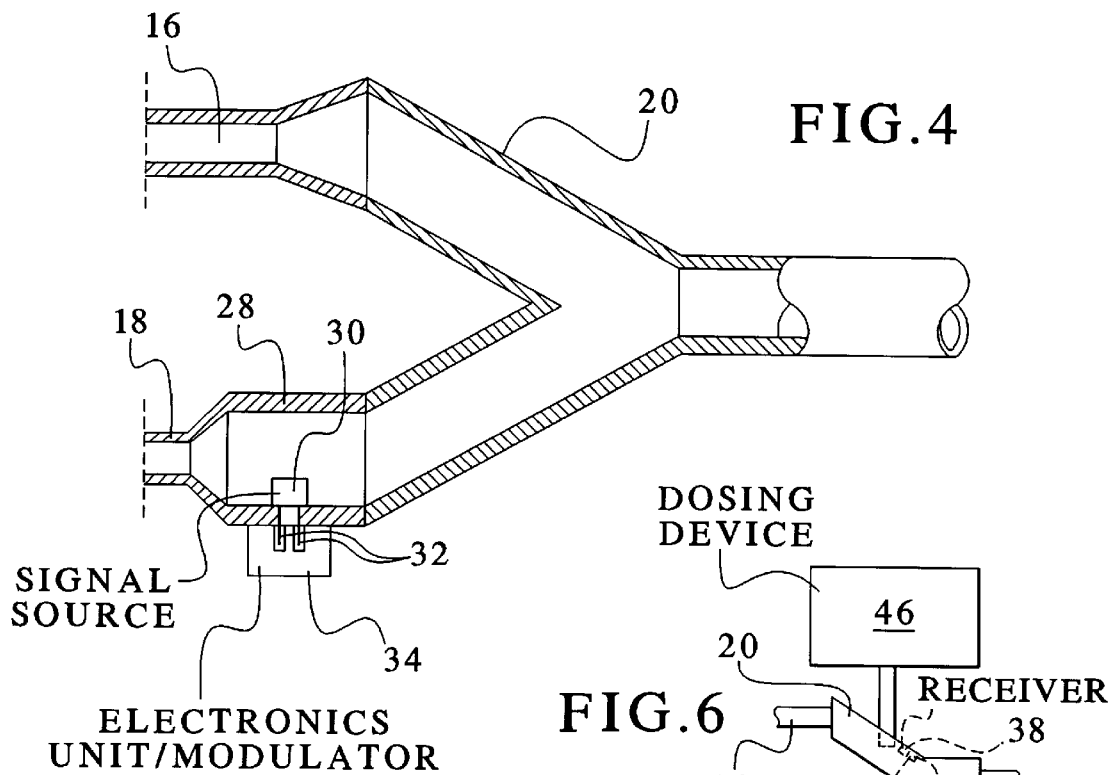
FIG. 4 shows an enlarged section of a Y-piece in which a signal source or receiver is arranged in accordance with the invention.

FIG. 1 shows a tube 2 leading to intensive care (such as breathing assist) or anesthesia equipment (not shown). At the patient end of the tube 2, a signal source in the form of an ultrasound transmitter 4 is arranged inside the tube 2, and an ultrasound receiver 6 is arranged at the machine end of the tube 2. From the patient end, the ultrasound transmitter 4 emits information-carrying signals, which pass through the medium contained inside the tube 2, such as anaesthetic gas, to the machine end of the tube 2 where the signals are received by the receiver 6.

The ultrasound transmitter 4 includes an ultrasound actuator, such as a crystal, which is electrically or mechanically excited. In the simplest version, the transmitter 4 can be controlled by a control element in the form of, for example, a push button, located on the exterior of the tube 2, for turning the transmitter 4 on and off. The transmitter 4 can alternatively be electronically controlled in a more sophisticated way, as described below.

Ultrasound propagates with low attenuation in most anesthetic gases, however, the attenuation increases in nitrous oxide, especially for frequencies above 100 kHz. For this reason, the selected ultrasonic frequency is preferably less than 100 kHz, as noted above, e.g. 40 kHz. A good range of transducers/transmitters is also commercially available for this frequency. For such a relatively low frequency as 40 kHz, the decay time of the crystal will be rather long, which limits the maximum rate of information transfer. In the present application, however, the amount of transmitted information is limited, so the reduced transfer rate is unimportant.

As schematically shown in FIG. 1a, the ultrasound transmitter 4 can be a tuning fork-type resonator 4b operable, for example, by a mode-selectable driver 4a in a fundamental oscillation mode or in a harmonic oscillation mode, so as to produce two (or more) tones.

The ultrasound transmitter 4 can also be connected to a transducer for transmitting information signals representing a measured quantity.

Signals picked up by the receiver 6 are sent to the intensive care or anesthetic machine for control purposes.

FIG. 2 illustrates the principle for an alternative version of the device according to the invention, in which an infrared light transmitter, such as a light-emitting diode 8 or a laser diode 8a (FIG. 2a), is arranged inside the tube 2 at the patient end for emitting information-carrying infrared light signals. These signals propagate along the tube while being reflected against the interior walls of the tube, and a receiver 10 is arranged at the machine end of the tube 2 to receive the infrared light signal.

The transmitted light beam should have a relatively wide spread to ensure that it reaches the receiver. There is no risk of information being lost due to interference, since the rate of information transfer is low.

In both the principles described in connection with FIGS. 1 and 2 and 2a the communication or the signal transmission occurs in the interior of the patient tube and therefore will not interfere with any other equipment in the area. The tube is thus devised, and is made from appropriate material, so that the passage of either sound or light through the tube wall is prevented. No noise or other signals near the device can penetrate into the tube and interfere with the signal transmission or generate unintentional control signals, which could be harmful.

FIG. 3 schematically shows a patient 12 connected to a breathing assist (intensive care or anesthetic) machine 14 via an inspiratory tube 16 and an expiratory tube 18. The tubes 16 and 18 are connected to the patient 12 via a so-called Y-piece 20. A signal source 24 of the above-described kind is arranged in the Y-piece 20 at the patient end of the tubes 16 and 18, and a receiver 26 is arranged at the machine end of the expiratory tube 18. In principle, the signal source and the receiver can consist of similar components.

The tube 16 is the so-called inspiratory tube through which gas is supplied to the patient 12, and the tube 18 is the so-called expiratory tube which carries gas from the patient back to the intensive care or anesthetic machine 14. For hygienic reasons, the signal source 24 and the receiver 26 are preferably arranged in the expiratory tube 18.

The signal source 24 is controlled by an operator near the patient (or alternatively by a transducer placed next to the patient), and the signal picked up by the receiver 26 is used for controlling the operation of the machine 14.

FIG. 4 shows, in a larger scale an intermediate piece 28 between the Y-piece 20 at the patient end and the expiratory tube 18. A signal source 30 is permanently mounted on the inner side of the intermediate piece 28, and from the source 30 contact pins 32 pass through the wail of the intermediate piece 28 for connection to an electronics unit 34 arranged on the exterior of the intermediate piece 28. The electronics unit 34 at the patient end of the tube is battery-powered and is attachable to the intermediate piece 28 with a snap fastener, so it can be easily detached together with its battery from the intermediate piece 28, whereupon the intermediate piece 28 with signal source 30 and contact pins 32 can be autoclaved.

Alternately, the electronics unit 34 and the battery can be made autoclavable.

The electronics unit 34 can be made small and light. Its volume does not need to exceed 20 cm$^3$ and its weight does not need to exceed 20 g, including the battery.

Instead of controlling the signal source by manual operating means, such as a push button, in this instance the signal source 30 is controlled electronically to permit more sophisticated signal transmission. The electronics unit 34 includes a modulator circuit so that transmitted signal can be modulated, e.g. frequency modulated, amplitude modulated, phase modulated or time modulated, and the CRC-sum (Cyclic Redundancy Check) of the data quantity can be calculated and appended to the end of the data word or words to increase reliability in signal transmission.

The signal source in the Y-piece 20 can be operated from the outside by an acoustic connection formed by an acoustic medium, instead of being operated by an external electronics unit via contact pins, as described above. Such an acoustic connection can consist of a single contact pin.

The gas flow in the tube may have an attenuating effect on the signal, and the transit time of the ultrasonic wave could theoretically be affected by the flow and type of gas. The typically encountered flow rates are so low, however, that this effect is negligible in the present application.

The electronics for the receiver at the machine end of the tube are appropriately supplied with power by the intensive care or anesthetic machine. No battery is then necessary.

Figure 5:
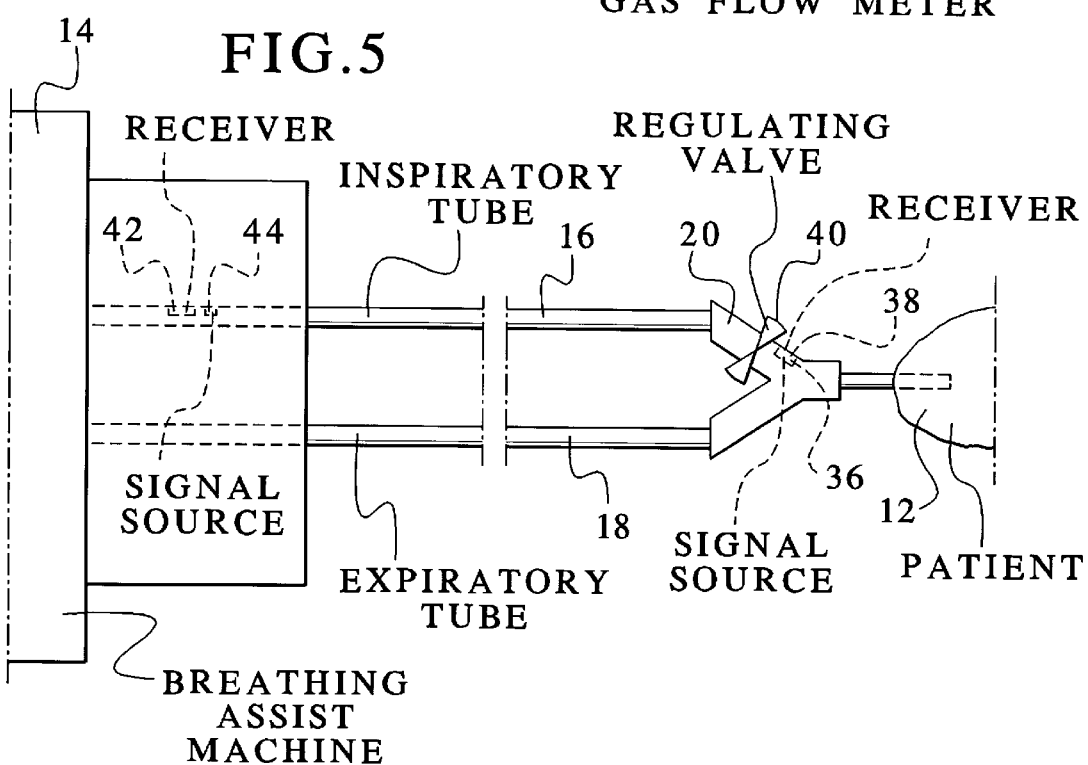
FIG. 5 shows an equipment similar to that in FIG. 3, equipped with a device according to the invention for two-way signal transmission.

FIG. 5 shows an embodiment similar to the one shown in FIG. 3, intended for two-way communication, or signal transfer, between the patient 12 and the machine 14.

A signal source 36, controlled by a measurement transducer, and a receiver 38 are arranged in the Y-piece 20 at the patient end. The receiver 38 controls a regulatory valve 40 according to the received signal.

A receiver 42 for receiving signals from the signal source 36 and an additional signal source 44 for transmitting signals to be received by the receiver 38 at the patient end are also arranged at the machine end. In this way two-way communication or signal transmission is possible between the patient end and the machine end.

The signal source and the receiver can be realized by a single crystal in the Y-piece 20 at the patient end and the machine end respectively, i.e. the same crystal can serve both as a transmitter and a receiver.

The measurement transducer by the signal source 36 can be, e.g., a flow meter which senses the inflow to the patient. The signal source 36 emits a corresponding measurement signal which is picked up by the receiver 42 in the machine 14, the machine 14 then delivering a control signal, via its signal source 44, to the regulating valve 40 for adjusting the flow 5 to the desired value. In this way a self-regulating feedback supply system is achieved.

The flow in the tube can also be determined from the Doppler shift caused by the flow of the medium. The signal sources at both ends of the tube are then suitably disposed or controlled to emit signals of the same frequency to be picked up by the respective receiver at opposite ends of the tube. The flow is then determined from the shift in frequency between the signals received by the receivers at the opposite ends of the tube. A separate flow meter is consequently not required in this embodiment.

Instead of controlling a regulating valve 40 at the patient end, other devices situated at the patient end, such as, e.g., a device for dosing medication or anesthetic, can be controlled in the same way.

Figure 6:
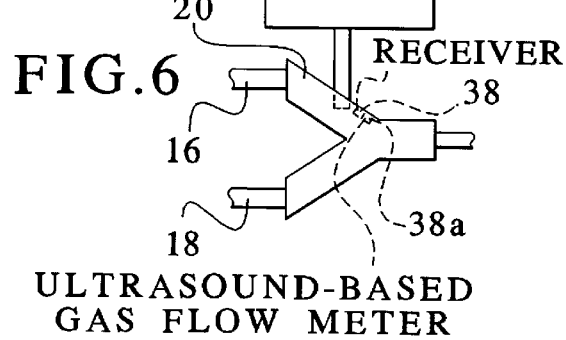
FIG. 6 shows a Y-piece arrangement substitutable for the Y-piece arrangement shown in FIG. 5, for use with a dosing device.

Other variations are also possible. Thus, e.g. as shown in FIG. 6, the receiver 38 at the patient end can be combined with an ultrasound-based gas flow meter 38a in order to realize a feedback, or pure safety monitoring, of gas supplied to the patient by a dosing device 46, which is a part of the breathing assist device 14. The version shown in FIG. 6 operates the same as that of FIG. 5, only the regulating valve 40 is replaced by the dosing device 46. The feedback can take place directly to the dosing device 46, in which case the receiver 42 and the signal source 44 (shown in FIG. 5) will be located at the dosing device 46, or feedback can take place as shown in FIG. 5, in which case a control line from the breathing assist device 14 to the dosing device 46 will be present. A specific dose to the patient can then also be set from the breathing assist device 14.

In the above-described embodiments, the signal transmission is based on ultrasound or infrared light techniques, but the device according to the invention can also be based on signal transmission with audible sound or visible light. In the case of communication by light transmission, i.e. infrared or visible, an optical conductor can also be incorporated into the tube wall for the signal transmission.

A gaseous medium in the tube is usual, but the device according to the invention could obviously also be used when the transmitting medium is a liquid.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical system comprising medical equipment, a patient tube having a first end remote from said medical equipment and a second end proximate said medical equipment and containing a fluid medium and a device for transmitting information via said patient tube for communicating with said medical equipment, said device comprising signal source means disposed at said first end of said tube for emitting signals carrying information into said fluid medium, said signals propagating longitudinally through said fluid medium inside said tube, and receiver means disposed at said second end of said tube for receiving said signals and for communicating said information carried by said signals to said medical equipment.

2. A medical system as claimed in claim 1 wherein said signal source means comprises an ultrasound source disposed inside said tube, and control means, disposed at an exterior of said tube, for controlling said ultrasound source.

3. A medical system as claimed in claim 1 wherein said signal source means comprises an ultrasound transducer disposed inside of said tube and an electronics unit connected to said ultrasound transducer and detachably mounted at an exterior of said tube.

4. A medical system as claimed in claim 3 wherein said tube has a tube wall, and said tube further comprising contact pins passing through said tube wall and connecting said ultrasound transducer to said electronics unit.

5. A medical system as claimed in claim 3 comprising an acoustic medium connecting said ultrasound transducer to said electronics unit.

6. A medical system as claimed in claim 3 wherein said electronics unit comprises a battery-powered electronics unit.

7. A medical system as claimed in claim 3 wherein said ultrasound transducer comprises an electrically excitable acoustic actuator.

8. A medical system as claimed in claim 3 wherein said ultrasound transducer comprises a mechanically excitable acoustic actuator.

9. A medical system as claimed in claim 3 wherein said ultrasound transducer comprises an ultrasound transducer operable at a frequency less than 100 kHz.

10. A medical system as claimed in claim 1 wherein said signal source means comprises an infrared light source which emits infrared light, and wherein said tube has an interior tube wall which reflects said infrared light.

11. A medical system as claimed in claim 10 wherein said infrared light source comprises an infrared transducer, and an electronics unit connected to said infrared transducer and detachably mounted at an exterior of said tube.

12. A medical system as claimed in claim 11 wherein said infrared transducer comprises a light-emitting diode.

13. A medical system as claimed in claim 11 wherein said infrared light transducer comprises a laser diode.

14. A medical system as claimed in claim 1 wherein said signal source means comprises means for emitting said information-carrying signal in the form of a modulated signal, modulated according to modulation selected from the group consisting of frequency modulation, amplitude modulation, phase modulation and time modulation.

15. A medical system as claimed in claim 1 wherein said signal source means comprises an activatable mechanical tuning fork-type transducer.

16. A medical system as claimed in claim 15 wherein said tuning fork-type transducer comprises a tuning fork-type transducer which emits at least two tones.

17. A medical system as claimed in claim 1 wherein said second end of said tube, at which said receiver means are disposed, is connected to said medical equipment.

18. A medical system as claimed in claim 17 wherein said receiver means comprises means for powering said receiver means with power supplied from said medical equipment.

19. A medical system as claimed in claim 1 comprising an intermediate piece, connectable to said first end of said patient tube and adapted for connection to a patient, and wherein said signal source means is disposed in said intermediate piece.

20. A medical system as claimed in claim 1 wherein said medical equipment contains a dosing unit, and wherein said first end of said tube, at which said signal source means are disposed, is connected to said dosing unit, and wherein said second end of said patient tube, at which said receiver means are disposed, is disposed at a patient, and wherein said receiver means comprises means for controlling said dosing unit dependent on said signal emitted by said signal source means.

21. A medical system as claimed in claim 1 wherein said medical equipment comprise an anaesthetic apparatus, wherein said patient tube comprises an expiratory tube connected to said anaesthetic apparatus, and wherein said signal source means and said receiver means are disposed in said expiratory tube.

22. A medical system as claimed in claim 1 wherein said medical equipment comprise a breathing assist apparatus, wherein said patient tube comprises an expiratory tube connected to said breathing assist apparatus, and wherein said signal source means and said receiver means are disposed in said expiratory tube.

23. A medical system as claimed in claim 1 further comprising further signal source means disposed at said second end of said tube for emitting a further information-carrying signal into said medium, said further information-carrying signals propagating through said medium inside said tube in a direction opposite to said information-carrying signal, and further receiver means, disposed at said first end of said patient tube, for receiving said further information-carrying signal.

24. A medical system as claimed in claim 23 wherein said medical equipment comprises equipment selected from the group consisting of a breathing assist apparatus and an anesthetic apparatus, wherein said medical equipment includes a controllable valve disposed at said first end of said patient tube and said first end of said patient tube is adapted for connection to a patient, and wherein said second end of said patient tube is connected to said medical equipment, and further comprising:

a flow meter disposed at said first end of said patient tube for measuring flow in said patient tube and for emitting an electrical flow signal corresponding to said flow to said signal source means;

said signal source means comprising means for converting said electronic flow meter signal into said information-carrying signal, which is received by said receiver means;

said further signal source means comprising means for emitting a control signal in said further information-carrying signal, which is received by said further receiver means; and said further receiver means comprising means for emitting an electrical control signal for controlling said controllable valve dependent on said control signal in said further information-carrying signal.

25. A medical system as claimed in claim 23 wherein said signal source means comprises means for emitting said information-carrying signal at a frequency and wherein said further signal source means comprises means for emitting said further information-carrying signal at the same frequency as said information-carrying signal, and further comprising means for determining flow in said tube from a shift in frequency between the information-carrying signal received by said receiver means and the further information-carrying signal received by said further receiver means.

* * * * *